United States Patent
Moser et al.

(10) Patent No.: US 9,079,817 B2
(45) Date of Patent: *Jul. 14, 2015

(54) INITIAL HYDROTREATING OF NAPHTHENES WITH SUBSEQUENT HIGH TEMPERATURE REFORMING

(75) Inventors: Mark D. Moser, Elk Grove Village, IL (US); David A. Wegerer, Lisle, IL (US); Manuela Serban, Glenview, IL (US); Kurt M. VandenBussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 264 days.

This patent is subject to a terminal disclaimer.

(21) Appl. No.: 13/327,220

(22) Filed: Dec. 15, 2011

(65) Prior Publication Data
US 2013/0158317 A1   Jun. 20, 2013

(51) Int. Cl.
| | |
|---|---|
| C10G 35/04 | (2006.01) |
| C07C 5/02 | (2006.01) |
| C07C 15/00 | (2006.01) |
| C10G 35/00 | (2006.01) |
| C10G 59/00 | (2006.01) |

(52) U.S. Cl.
CPC ............... C07C 15/00 (2013.01); C10G 35/00 (2013.01); C10G 59/00 (2013.01); C10G 2400/30 (2013.01)

(58) Field of Classification Search
CPC ............. C07C 5/00; C07C 5/02; C07C 5/03; C07C 5/32; C07C 5/321; C07C 5/324; C07C 5/325; C07C 4/00; C07C 4/02; C07C 4/04; C07C 4/06; C10G 35/00; C10G 35/02; C10G 35/04; C10G 35/06; C10G 35/085; C10G 35/09

USPC ......... 585/300–304, 312, 315, 319, 322, 407, 585/430, 800, 804, 805
See application file for complete search history.

(56) References Cited

U.S. PATENT DOCUMENTS

| | | | | |
|---|---|---|---|---|
| 4,401,554 | A * | 8/1983 | Choi et al. ............... | 208/64 |
| 4,508,617 | A | 4/1985 | Montgomery | |
| 5,935,415 | A * | 8/1999 | Haizmann et al. ....... | 208/64 |
| 6,004,452 | A * | 12/1999 | Ash et al. ................. | 208/80 |
| 6,740,228 | B1 * | 5/2004 | Verduijn et al. .......... | 208/138 |
| 2007/0299289 | A1 * | 12/2007 | Bresler et al. ........... | 585/323 |

FOREIGN PATENT DOCUMENTS

| | | |
|---|---|---|
| RU | 2417249 C1 | 4/2011 |
| WO | 1991006616 A2 | 5/1991 |

OTHER PUBLICATIONS

Sinnott, R.K, Coulson & Richardson's Chemical Engineering, Chemical Engineering Design, vol. 6, Fourth Edition, Elsevier, p. 50.*
U.S. Appl. No. 13/327,164, filed Dec. 15, 2011, Moser et al.
U.S. Appl. No. 13/327,200, filed Dec. 15, 2011, Moser et al.

(Continued)

Primary Examiner — In Suk Bullock
Assistant Examiner — Philip Louie

(57) ABSTRACT

A process for the production of aromatics through the reforming of a hydrocarbon stream is presented. The process utilizes the differences in properties of components within the hydrocarbon stream to increase the energy efficiency. The differences in the reactions of different hydrocarbon components in the conversion to aromatics allows for different treatments of the different components to reduce the energy used in reforming process.

16 Claims, 2 Drawing Sheets

(56) References Cited

OTHER PUBLICATIONS

U.S. Appl. No. 13/327,143, filed Dec. 15, 2011, Moser et al.
U.S. Appl. No. 13/327,212, filed Dec. 15, 2011, Moser et al.
U.S. Appl. No. 13/327,185, filed Dec. 15, 2011, Serban et al.
U.S. Appl. No. 13/327,178, filed Dec. 15, 2011, Serban et al.
U.S. Appl. No. 13/327,170, filed Dec. 15, 2011, Serban et al.
U.S. Appl. No. 13/327,192, filed Dec. 15, 2011, Serban et al.
U.S. Appl. No. 13/416,513 filed Mar. 9, 2012, Serban.
U.S. Appl. No. 13/416,702 filed Mar. 9, 2012, Gajda.
U.S. Appl. No. 13/417,181 filed Mar. 9, 2012, Gajda.
U.S. Appl. No. 13/417,200 filed Mar. 9, 2012, Wegerer.
U.S. Appl. No. 13/417,202 filed Mar. 9, 2012, Gajda.
U.S. Appl. No. 13/417,203 filed Mar. 10, 2012, Gajda.
U.S. Appl. No. 13/440,487 filed Apr. 5, 2012, Moser.
U.S. Appl. No. 13/440,527 filed Apr. 5, 2012, Moser.
U.S. Appl. No. 13/440,381 filed Apr. 5, 2012, Moser.
U.S. Appl. No. 13/428,005 filed Mar. 23, 2012, Serban.
U.S. Appl. No. 13/416,604 filed Mar. 9, 2012, Serben.
U.S. Appl. No. 13/416,577 filed Mar. 9, 2012, Negiz.
PCT International Preliminary Report on Patentability for PCTUS2012/055014, mailing date 26 Jun. 2014, Applicant reference.

* cited by examiner

INITIAL HYDROTREATING OF NAPHTHENES WITH SUBSEQUENT HIGH TEMPERATURE REFORMING

FIELD OF THE INVENTION

The present invention relates to the process of enhancing the production of aromatic compounds. In particular the improvement and enhancement of aromatic compounds such as benzene, toluene and xylenes from a naphtha feedstream through high temperature reforming.

BACKGROUND OF THE INVENTION

The reforming of petroleum raw materials is an important process for producing useful products. One important process is the separation and upgrading of hydrocarbons for a motor fuel, such as producing a naphtha feedstream and upgrading the octane value of the naphtha in the production of gasoline. However, hydrocarbon feedstreams from a raw petroleum source include the production of useful chemical precursors for use in the production of plastics, detergents and other products.

The upgrading of gasoline is an important process, and improvements for the conversion of naphtha feedstreams to increase the octane number have been presented in U.S. Pat. No. 3,729,409, U.S. Pat. No. 753,891, U.S. Pat. No. 767,568, U.S. Pat. No. 839,024, U.S. Pat. No. 882,040 and U.S. Pat. No. 242,576. These processes involve a variety of means to enhance octane number, and particularly for enhancing the aromatic content of gasoline.

While there is a move to reduce the aromatics in gasoline, aromatics have many important commercial uses. Among those commercial uses include the production of detergents in the form of alkyl-aryl sulfonates, and plastics. These commercial uses require more and purer grades of aromatics. The production and separation of aromatics from hydrocarbons streams are increasingly important.

Processes include splitting feeds and operating several reformers using different catalysts, such as a monometallic catalyst or a non-acidic catalyst for lower boiling point hydrocarbons and bi-metallic catalysts for higher boiling point hydrocarbons. Other improvements include new catalysts, as presented in U.S. Pat. No. 4,677,094, U.S. Pat. No. 6,809,061 and U.S. Pat. No. 7,799,729. However, there are limits to the methods and catalysts presented in these patents, and which can entail significant increases in costs.

Improved processes are needed to reduce the costs and energy usage in the production of aromatic compounds.

SUMMARY OF THE INVENTION

The present invention has found that the production of aromatics from a hydrocarbon stream, such as a full boiling range naphtha, with a substantial amount of naphthenic compounds. Processing the feedstream, or a portion of the feedstream, to reduce the naphthenes to aromatics before reforming the process stream reduces the energy load on the reforming units and increases the aromatics content in the product stream.

The process separates the hydrocarbon feedstream into two streams, one with an increased naphthene content, and one with a reduced naphthene content. The process includes passing the hydrocarbon feedstream to a fractionation unit to generate an overhead stream and a bottoms stream. The overhead stream comprises C7 and lighter hydrocarbons, including naphthenes, and the bottoms stream comprises C8 and heavier hydrocarbons. The overhead stream is passed to a dehydrogenation unit to generate a dehydrogenated stream with a reduced naphthene content. The bottoms stream is passed to a first reactor system to generate a first effluent stream. The first effluent stream and the dehydrogenated stream are passed to a second reforming reactor system to generate an aromatics effluent stream. The aromatics effluent stream is passed to a reformate splitter to generate an overhead stream comprising C7 and lighter aromatics and hydrocarbons, and a bottoms stream comprising C8 and heavier hydrocarbons. The reformate overhead stream is passed to an aromatics recovery unit to generate an aromatics product stream comprising benzene and toluene.

Other objects, advantages and applications of the present invention will become apparent to those skilled in the art from the following detailed description and drawings.

DETAILED DESCRIPTION OF THE INVENTION

The reforming of a hydrocarbon feedstream to increase the aromatics content is important for enhancing the value of the hydrocarbon stream. Aromatics, such as benzene and toluene are high value chemicals and are used in a variety of processes to generate downstream products. Examples include alkylaromatic compounds for detergents, ethyl benzene and cumene. The reforming process can include endothermic reactions and can affect the efficiency due to process control of the temperatures of the reactors.

The present invention is directed to improving the yields of aromatics from a hydrocarbon feedstream. In particular, the improvement is for a full boiling range naphtha feedstream where the hydrocarbons are reformed to increase the yields of aromatics in the C6 to C8 range. The new process is designed to utilize a multiple reactors, controlled at different conditions to maximize paraffin cyclization and aromatization, but also minimize metal-catalyzed coking and thermal cracking. Due to problems associated with high inlet temperatures, it is desirable to maximize the catalyst bed temperatures while minimizing the reactor inlet temperatures. Due to the endothermic nature of some of the components in a naphtha feed, the usual approach is to heat the feed to a greater temperature, as the temperature will drop in the reactor.

It is significant to note that in studying the reforming process, it is generally known that larger paraffins, such as C8 and larger, aromatize more readily than C6 paraffins. This would lead to the belief that the lighter hydrocarbons would benefit from longer residence times in the reactor than larger paraffins. Contrary to this, it was found that applying shorter contact times for the lighter hydrocarbons than for the heavier hydrocarbons produced greater overall conversion yields. This leads to new ideas on the process control that are counter-intuitive to the accepted reforming process.

Figure 1:
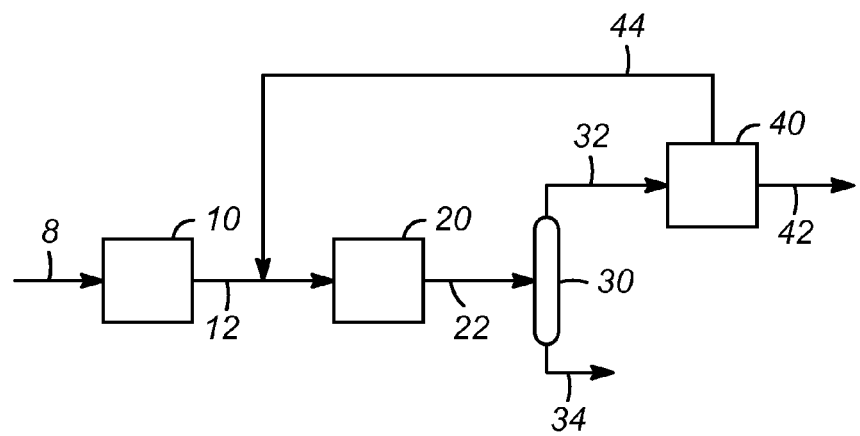
FIG. 1 shows one embodiment of the present invention with a dehydrogenation reactor applied to the total feed, followed by reforming reactors.

The present invention seeks to improve the energy savings of the reforming process of a hydrocarbon feedstream in the production of aromatic compounds. The process, as shown in FIG. 1, includes passing a hydrocarbon feedstream 8 to a first reactor 10 to generate a dehydrogenated hydrocarbon stream 12. The first reactor is for hydrotreating the naphthenic compounds, and can be either a dehydrogenation reactor, or a reforming reactor. When the first reactor is a reforming reactor, the same catalyst can be used in each of the reforming reactors in the process described herein. The dehydrogenated stream 12 is passed to a second reactor system 20 to generate a reformed hydrocarbon stream 22 having an increased aromatics content. The second reactor system is preferable a reforming reactor system that is operated at substantially isothermal conditions. The reforming reactor system 20 cyclizes and aromatizes the paraffinic compounds. The dehydrogenated hydrocarbon stream has a reduced naphthene content, and allows for lower energy input to subsequent reactors, and allows for operating the isothermal reactor system 20 at an increased temperature while minimizing the temperature drop in the reactors. The reformed hydrocarbon stream 22 is passed to a reformate splitter 30 to generate a reformate overhead stream 32 having C6 and C7 aromatics, and a reformate bottoms stream 34 having heavier hydrocarbons. The reformate overhead is passed to an aromatics separation unit 40 to generate an aromatics product stream 42 and a raffinate stream 44. The raffinate stream 44 can be directed back to the reforming reactor system 20 to further cyclize and aromatize the paraffins in the raffinate stream 44.

The aromatics recovery unit 40 can comprise different methods of separating aromatics from a hydrocarbon stream. One industry standard is the Sulfolane™ process, which is an extractive distillation process utilizing sulfolane to facilitate high purity extraction of aromatics. The Sulfolane™ process is well known to those skilled in the art.

The dehydrogenation reactor system 10 can comprise a plurality of reactors, where each reactor is operated at a temperature between 200° C. and 650° C., with a preferred operation temperature between 440° C. and 560° C. Operational conditions for the dehydrogenation reactor include a pressure between 100 kPa and 10 MPa, with a preferred pressure between 100 kPa and 2 MPa, and with a more preferred pressure between 100 kPa and 500 kPa. The dehydrogenation reactor system 10 can include a recycle hydrogen gas stream for the dehydrogenation process.

The substantially isothermal reactor system 20 comprises a plurality of reactors with inter-reactor heaters, and can include a temperature step up reactor system, where first one or two reactors in the system are operated at a lower temperature, with the remainder of the reactors operated at higher temperatures. The reactors are operated in a series arrangement, where the process stream flows through each reactor, and is reheated to the same inlet reactor temperature for each reactor. The reforming reactor system 20 is preferably operated at a temperature of at least 540° C., with the reforming reaction temperature conditions between 540° C. and 600° C., and more preferably between 560° C. and 580° C.

When the reforming system 20 is operated in a temperature step up mode, the first reactor, or first and second reactors, are operated at a temperature between 440° C. and 560° C., and the subsequent reactors operated at a temperature greater than 540° C. Preferably the first reactor is operated at a temperature between 440° C. and 460° C., with the subsequent reactors operated at a temperature between 550° C. and 570° C. One optional operation of the reforming reactor system 20 is to operate each subsequent reactor at a higher temperature than the previous reactor in the series.

In addition to the operational temperatures, the processing conditions of the different reformers allows for different operational control. Additional variables that are controllable include the space velocities, the hydrogen to hydrocarbon feed ratios, and the pressures. It is preferred that the pressure in the reformer with the lighter hydrocarbons is operated at a lower pressure that in the reformer with the heavier hydrocarbons. An example for operating pressures for the first reformer are from 130 kPa to 310 kPa with a preferred pressure of around 170 kPa (10 psig), and operating pressures for the second reformer are from 240 kPa to 580 kPa with a preferred pressure of around 450 kPa (50 psig).

The simulation of a commercial reactor included an inlet temperature of 515° C. to 560° C., a hydrogen to hydrocarbon ratio of 5, pressures in the reactor at different levels from 10 to 50 psig, or 170 to 450 kPa, the WHSV ranged from 0.75 $hr^{-1}$ to 3 $hr^{-1}$, and with different catalyst loadings to expand the conversion range.

The reformate splitter 30 can be operated to change the mix of aromatics in the overhead stream 32. For an increase in xylene recovery, the reformate splitter 30 can be operated to send C8 aromatics into the overhead stream 32, and to the subsequent aromatics recovery unit 40.

Figure 2:
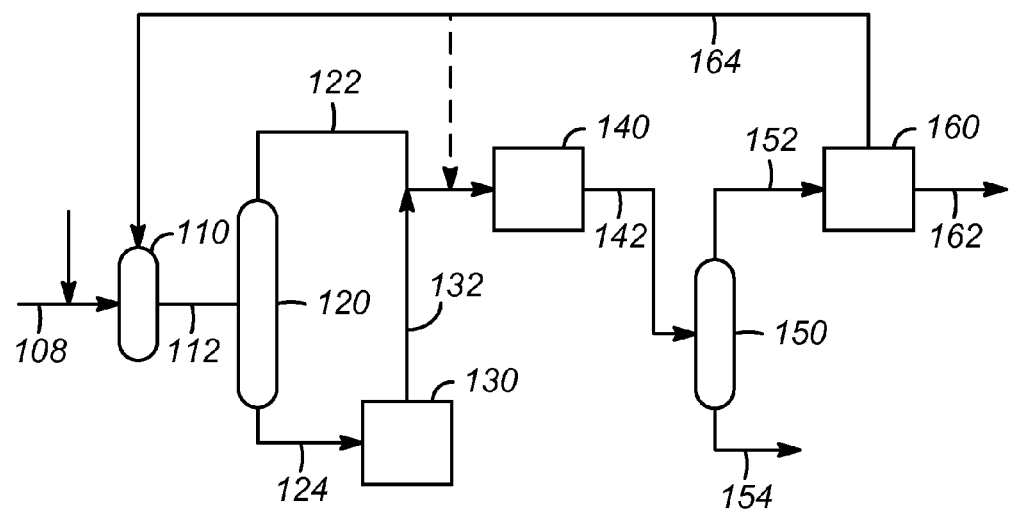
FIG. 2 shows a second invention where a hydrocarbon stream is dehydrogenated before passing the streams on to the reforming reactor system and the dehydrogenated stream is separated and reformed.

The process for another invention comprises passing a portion of a hydrocarbon feedstream, as shown in FIG. 2. In particular, a naphtha feedstream 108 is dehydrogenated in a dehydrogenation reactor 110 to generate a naphtha feedstream having a reduced naphthene content 112. The reduced naphtha stream 112 is passed to a fractionation unit 120 to generate a light overhead stream 122 comprising C7 and lighter hydrocarbons, and a heavy bottoms stream 124 comprising C8 and heavier hydrocarbons. The bottoms stream 124 is passed to a first reformer reactor system 130 to generate a first reformate stream 132 having an increased aromatics content. The first reformate stream 132 and the light overhead stream 122 are passed to a second reformer reactor system 140 to generate a second reformate stream 142 comprising aromatics. The second reformer reactor system 140 is operated as a substantially isothermal reactor system, and is operated at a high temperature. In an alternate embodiment, the reactor 110 can comprise a reforming reactor instead of a dehydrogenation reactor.

In one embodiment, the reduced naphtha stream 112 is passed to an off-gas separator (not shown) to remove light off-gases, such as hydrogen, and any residual acid gases, such as hydrogen sulfide, that is generated in the dehydrogenation reactor 110, before passing the naphtha stream 112 to the fractionation unit 120. The second reformate stream 142 is passed to a reformate splitter 150 to generate a reformate overhead stream 152 comprising C6 and C7 aromatics and lighter hydrocarbons, and a reformate bottoms stream 154 comprising C8 and heavier hydrocarbons. The reformate overhead stream 152 is passed to an aromatics recovery unit 160 to generate an aromatics product stream 162 and a raffinate stream 164. The aromatics product stream 162 will comprise benzene and toluene, and small amounts of xylenes. Optionally, the reformate splitter 150 can be operated to recover C8 aromatics in the reformate overhead stream 152 and subsequently in the aromatics product stream 162.

The first reformer reactor system 130 can comprise a plurality of reactors with inter-reactor heaters. In a preferred embodiment, the reactors are in a series relationship, with the first reformer reactor system 130 comprises two reactors with each reactor having a reactor feed heater. The first reactor is operated at a lower temperature and at conditions to convert the most endothermic hydrocarbons to aromatics. The first reactor product is heated to a higher inlet temperature for the second reactor. Temperatures for the first reactor have an inlet temperature between 440° C. and 560° C., with a preferred inlet temperature between 440° C. and 460° C., with a more preferred temperature between 445° C. to 455° C., and a most preferred inlet temperature of 450° C. Temperatures for the second reactor have an inlet temperature between 540° C. and 580° C., with a preferred inlet temperature of 560° C. The second reformer reactor system 140 can comprise a plurality of reactors in a series relationship with inter-reactor heaters. When operated in conjunction with the first reactor system 130, the second reactor system 140 is operated to control the temperature so as to minimize temperature variation. In particular, the reactions are endothermic, so the inter-reactor heaters are operated to heat the reactor inlet temperatures to between 540° C. and 580° C., with a preferred inlet temperature of 560° C.

In one embodiment, the raffinate stream 164 is passed to the first reactor in the first reactor system 140, to cyclize and aromatize the more endothermic components, before passing the first reactor effluent on to a subsequent reactor.

One specific embodiment includes passing a naphtha feedstream 108 and a hydrogen rich recycle gas to the dehydrogenation reactor 110 to reduce the naphthenic content of the naphtha feedstream 108. The reduced stream 112 is passed to a fractionation unit 120 to generate a C7 and lower hydrocarbon stream 122, and a C8 and heavier hydrocarbon stream 124. The C8 and heavier hydrocarbon stream 124 is passed with recycle gas to a first reactor system 130 to generate a first reactor effluent stream 132. The first reactor effluent stream 132 and the C7 and lower hydrocarbon stream 122 are passed to a second reactor system 140 to generate a second reactor effluent stream 142. The second reactor effluent stream 142 is passed to a reformate splitter 150 to generate a reformate overhead 152 and a reformate bottoms stream 154. The reformate overhead 152 comprises C6 and C7 aromatics and is passed to an aromatics recovery unit 160 to generate an aromatics product stream 162 and a raffinate stream 164. The raffinate stream 164 is passed to the dehydrogenation reactor 110 to react the olefins and reduce the amount of olefins passed to the reforming reactor systems 130 and 140.

In another embodiment, the process for increasing the aromatics yields from a hydrocarbon feedstream includes passing the hydrocarbon stream to a dehydrogenation reactor. The dehydrogenated stream is passed to a separator to create a light hydrocarbon stream comprising C7 and lighter hydrocarbons, and a heavy hydrocarbon stream comprising C8 and heavier hydrocarbons. The light stream is passed to a first reforming reactor system to generate a first reformate stream, comprising C6 and C7 aromatic compounds. The heavy stream is passed to a second reforming reactor system to generate a second reformate stream comprising aromatic compounds. The first and second reformate streams are passed to a reformate splitter to generate an overhead stream comprising C7 and lighter aromatics and hydrocarbons, and a bottoms stream comprising C8 and heavier aromatics and hydrocarbons.

Figure 3:
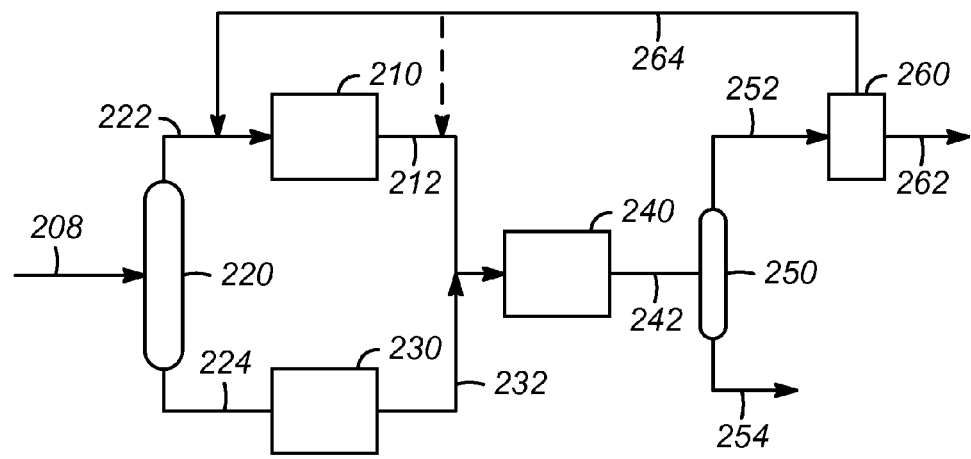
FIG. 3 shows another embodiment with a dehydrogenation reactor applied to the light ends of a fractionated feed.

The invention for increasing the yields of aromatics from a hydrocarbon feedstream involves improving the approach for reforming the hydrocarbon feedstream. While the process of reforming a hydrocarbon feedstream is known, and one of the issues is the endothermic nature of the process, there is no information that teaches one can improve the yields, while reducing energy consumption by a innovative method of processing the hydrocarbon stream. The process, as shown in FIG. 3, involves passing the hydrocarbon feedstream 208 to a fractionation unit 220. The feedstream is separated into a light overhead stream 222 and a heavier bottoms stream 224. The light overhead stream 222 comprises C7 and lighter hydrocarbons and is passed to a dehydrogenation reactor 210 where a dehydrogenated stream 212 having a reduced naphtene content is generated. The bottoms stream 224, comprising C8 and heavier hydrocarbons, is passed to a first reforming reactor system 230 to generate a first reactor effluent stream 232. The first effluent stream 232 and the dehydrogenated stream 212 are passed to a second reactor system 240 to generate an aromatics effluent stream 242.

In an alternate embodiment to the process as shown in FIG. 3, the reactor 210 can comprise a reforming reactor instead of a dehydrogenation reactor. The benefit of using a reforming reactor, operated at a lower temperature, provides for the use of the same catalyst in all of the reforming reactors.

The process can further include passing the aromatics effluent stream 242 to an aromatics splitter 250 to generate an aromatics overhead stream 252 having C7 and lighter aromatics, and a bottoms stream 254 having heavier hydrocarbons. The aromatics overhead stream 252 is passed to an aromatics separation unit 260 to generate an aromatics product stream 262 and a raffinate stream 264. The raffinate stream 264 can have a substantial amount of olefins in the raffinate, and can be passed to the dehydrogenation reactor 210 for further processing of the olefins and conversion to aromatics. When the raffinate stream 264 is low in olefin content, the raffinate stream 264 can bypass the dehydrogenation reactor and be passed to the second reactor system 240.

The first reactor system 230 can include a plurality of reactors, where each reactor has a heater for heating the incoming process fluid to a desired reaction temperature. The reactors are operated in a series arrangement, with inter-reactor heaters. In the first reactor system 230, the first reactor within the system 230, the first reactor is operated at an inlet temperature between 440° C. and 560° C., and preferably between 440° C. and 460° C. Subsequent reactors in the first reactor system are operated with an inlet reactor temperature between 540° C. and 580° C., and preferably with an inlet temperature between 560° C. and 580° C.

The second reactor system 240 can include a plurality of reactors in a series arrangement, with each reactor having a heater for controlling the inlet temperature of the processing fluid. The inlet temperature for each reactor is in the temperature range from 540° C. to 580° C., with a preferred range from 560° C. to 580° C., and with a more preferred control of the inlet temperature to 560° C.

Figure 4:
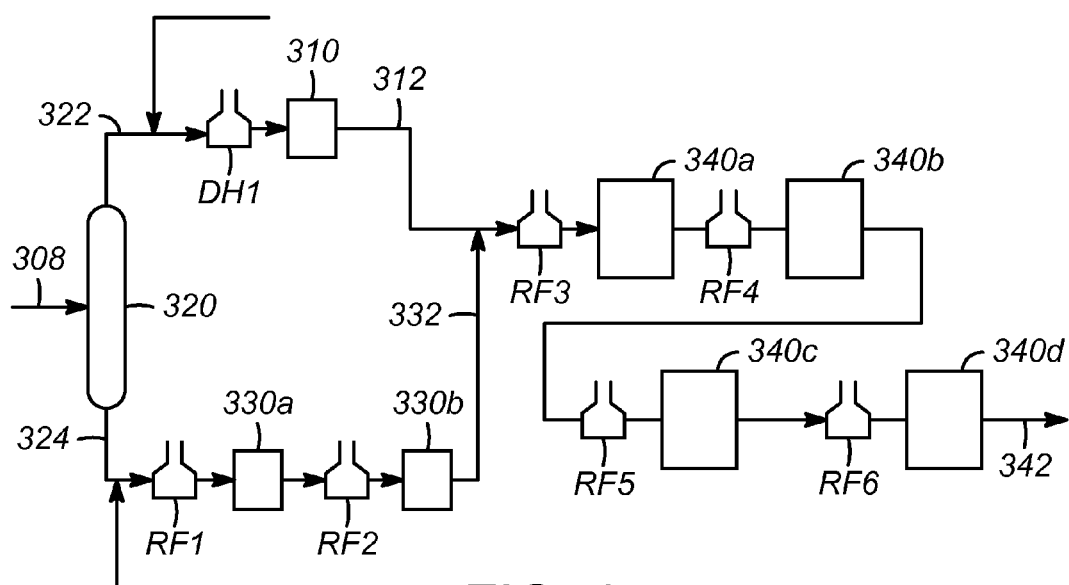
FIG. 4 shows a specific configuration with a six reactor system.

Using microreactor results, and simulations, the heat and weight balances for reactor configurations were tested. FIG. 4 shows a combination of six reactor beds with a dehydrogenation reactor 310 for treating the overhead stream 322 from the fractionation unit 320. The six reactor beds are in a 2×4 configuration with 2 reactors in the first reactor system, and 4 reactors in the second reactor system. A comparison of heat and weight balance results and reformate yields for the naphtha reforming processes was performed between this case and a case where there was no dehydrogenation reactor 310. Each reactor has a feed heater, where the feed into each reactor was raised to a preferred temperature. In the process, the naphtha feed 308 is split to produce an overhead stream 322 rich in C7 naphthenes and lighter components and a bottoms stream 324 rich in C8 and heavier components. The bottoms stream 324 is fed to the first reforming catalyst reactor 330a, with the effluent from the first reforming reactor 330a fed to the second reforming reactor 330b to generate a first stream 332. The overhead stream 322 is fed to the dehydrogenation reactor 310 to generate the dehydrogenated effluent stream 312. The dehydrogenated stream 312 and the first stream 332 are combined and heated in RF3 to be fed to the third reforming reactor 340a. The process stream subsequently passed through the subsequent reactor feed heaters RF4, FR5, RF6 and subsequent reactors 340b, 340c, and 340d as shown in FIG. 4.

TABLE 1

Reforming Reactor Inter-Heater Duty (MM Btu/hr)

| | Split Naphtha Feed and 2 + 4 Series Flow Reforming Section | Split Naphtha Feed with Light Naphtha Dehydro and 2 + 4 Series Flow Reforming Section |
|---|---|---|
| Reactor 2 Feed Heater | 133.10 | 132.70 |
| Reactor 3 Feed Heater | 120.00 | 119.80 |
| Reactor 4 Feed Heater | 83.29 | 69.19 |
| Reactor 5 Feed Heater | 51.65 | 44.28 |
| Reactor 6 Feed Heater | 29.02 | 24.16 |

The 2+4 reforming reactor section comprises six reactors in series, with the heavy hydrocarbon stream passing through the first two reactors, and with the light hydrocarbon stream merging with the second reactor effluent and passing through the remaining 4 reactors. The heat duties are in MM Btu/hr.

From the results, the process that includes the naphthene dehydrogenation upstream of the reforming reactors results in a lower heat duty for inter-reactor heaters (RF3, RF4, RF5 and RF6). In addition, the following Table 2, shows the dehydrogenation pre-treatment of the naphtha feedstream results in a reduced temperature drop in the reactors. This is due to the reduction in the reaction endotherm in the reactor beds due to a reduction in the amount of naphthenes passing to the reforming reactors. This provides for keeping the system nearer to an isothermal process, with the reactions held nearer to the desired reaction temperature.

TABLE 2

Reforming Zone Reaction Conditions

| | Split Naphtha Feed and 2 × 4 Series Flow Reforming Section | | | Split Naphtha Feed with Light Naphtha Dehydro and 2 × 4 Series Flow Reforming Section | | |
|---|---|---|---|---|---|---|
| | R × R vol. | R × R inlet | R × R outlet | R × R vol. | R × R inlet | R × R outlet |
| Reactor 1 | 13.11 | 449 | 417 | 13.11 | 449 | 417 |
| Reactor 2 | 18.12 | 560 | 475 | 18.12 | 560 | 475 |
| Reactor 3 | 17.53 | 560 | 497 | 17.53 | 560 | 507 |
| Reactor 4 | 18.75 | 560 | 520 | 18.75 | 560 | 527 |
| Reactor 5 | 19.28 | 560 | 538 | 19.28 | 560 | 542 |
| Reactor 6 | 19.43 | 560 | 549 | 19.43 | 560 | 551 |

Reactor volume (R×R vol.) is in cubic meters, and temperatures are in degrees Celsius. The inlet temperature for the first reactor is 449° C. and for the remaining reactors is 560° C.

While this provides a significant energy savings, there is an improvement in the conversion of the naphtha feed to aromatics by maintaining higher reactor temperatures. Table 3 shows the increase in the yields of benzene (A6) and toluene (A7) with the inclusion of the dehydrogenation reactor 310. The improvement in yields are due in part to the higher overall reactor temperatures in the reforming reactors.

TABLE 3

Reformate Composition and Aromatics Yields

| Split Naphtha Feed and 2 × 4 Series Flow Reforming Section | | Split Naphtha Feed with Light Naphtha Dehydro and 2 × 4 Series Flow Reforming Section | |
|---|---|---|---|
| Net Reformate | | Net Reformate | |
| H2, % | 3.8 | H2, % | 3.9 |
| C1-C5, % | 16.5 | C1-C5, % | 16.7 |
| C6-C10, % | 79.7 | C6-C10, % | 79.3 |
| C11+, % | 0.1 | C11+, % | 0.1 |
| P6 Conversion w/w | 0.627 | P6 Conversion w/w | 0.610 |
| P7 Conversion w/w | 0.989 | P7 Conversion w/w | 0.982 |
| P8 Conversion w/w | 0.998 | P8 Conversion w/w | 0.998 |
| Net Reformate Aromatics | | Net Reformate Aromatics | |
| A6-A7, % | 25.2 | A6-A7, % | 25.9 |
| PX, w/w | 0.032 | PX, w/w | 0.032 |
| Total A6-A10 | 68.2 | Total A6-A10 | 68.9 |

The results of two simulations showing the improvement is shown in Tables 4 and 5. A base case was run, and compared against the new configuration.

TABLE 4

Same amount of catalyst

| | Base case | Case 1 |
|---|---|---|
| Reactor inlet temp, deg. C. | 560 | 468 and 560 |
| C7 paraffin conversion, w/w % | 97.8% | 97.9% |
| Total catalyst volume, m3 | 121.8 | 121.8 |
| Net Yield (A7-A10), w/w % | 52.4% | 52.9% |
| Net Yield (C1-C4), w/w % | 15.1% | 14.8% |
| Net Yield, H2, w/w % | 3.8% | 3.8% |

The cases presented in Table 3 include the new configuration, Case 1, against a base case. The base case involved the use of a reforming reactor system operated at a high temperature. In the base case, there were four reforming reactors with the inlet temperature of 560° C. The new configuration in Case 1, involved the reforming reactor system of the base case, with a pre-reactor. The pre-reactor was a reforming reactor operated at 468° C. The total amount of catalyst for both the base case and the new configuration was the same, where the catalyst was redistributed, such that each reactor in the new configuration has a smaller amount of catalyst. The process shows an increase in the yields of aromatics, while also having the added benefit of a decrease in yields of light ends. The net yield is equal to the net outlet minus the fresh feed divided by the fresh feed, or:

(Net Yield)=(Net Outlet−Fresh Feed)/(Fresh Feed).

A second simulation was run to show the improvement allows for a reduction in the amount of catalyst necessary to show improved yields.

TABLE 5

Reduced catalyst

| | Base case | Case 2 |
|---|---|---|
| Reactor inlet temp, deg. C. | 560 | 454 and 560 |
| C7 paraffin conversion, w/w % | 97.8% | 97.8% |
| Total catalyst volume, m3 | 121.8 | 84.95 |

TABLE 5-continued

Reduced catalyst

|  | Base case | Case 2 |
| --- | --- | --- |
| Net Yield (A7-A10), w/w % | 52.4% | 54.1% |
| Net Yield (C1-C4), w/w % | 15.1% | 13.2% |
| Net Yield, H2, w/w % | 3.8% | 4.0% |

The reduced catalyst shows there is improvement with using less catalyst. In case 2, the total amount of catalyst for all the reactors is over 30% less than the total amount of catalyst for the base case. In case 2, there were seven reactors operated at the high temperature of 560° C., and the pre-reactor operated at 454° C. The total catalyst was distributed over all of the reactors. The lower temperature in the pre-reactor provides the benefit of lower catalyst volume in the downstream reactors operated at the elevated temperature. The new process also has a higher space velocity, which reduces secondary reactions and also contributes to improved operations.

The reforming reactions were operated with a platinum catalyst. The platinum catalyst needs some metal passivation for the prevention of metal catalyzed coking during the process. The metal passivation is performed through the addition of a small amount of sulfur. The sulfur in the reactor is usually provided by hydrogen sulfide ($H_2S$). The $H_2S$ addition to the process is generated through the addition of DMDS (dimethyl disulfide) upstream of the reactors. The DMDS thermally decomposes during the heating of the feedstream. However, the DMDS is not entirely decomposed to $H_2S$ and some of the DMDS enters the reactors, and prematurely deactivates some of the catalyst in the high temperature process. An unexpected benefit with the new process includes the total decomposition of the DMDS to $H_2S$ in the pre-reactor, and thereby protects the catalyst in the high temperature reforming reactors.

Therefore, increases can be achieved through innovative flow schemes that allow for process control of the reactions. While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for increasing the yields of aromatics from a hydrocarbon feedstream, comprising:
    passing the hydrocarbon feedstream to a fractionation unit to generate an overhead stream comprising C7 and lighter hydrocarbons, and a bottoms stream comprising C8 and heavier hydrocarbons;
    passing the overhead stream to a dehydrogenation reactor to dehydrogenate naphthenes and generate a dehydrogenated stream having a reduced naphthenic content;
    passing the bottoms stream to a first reforming reactor system to generate a first reactor effluent having an increased aromatic content, wherein the first reforming reactor system is operated at an inlet temperature between 440° C. and 560° C.;
    passing the first reactor effluent to a second reforming reactor system, and the dehydrogenated overhead stream to the second reforming reactor system to generate an aromatics effluent stream, wherein the second reactor system is operated at an inlet temperature between 540° C. and 580° C. and a pressure less than 580 kPa.

2. The process of claim 1 further comprising:
    passing the aromatics effluent stream to an aromatics splitter to generate an aromatics overhead having C7 and lighter aromatics, and a bottoms stream; and
    passing the aromatics overhead stream to an aromatics separation unit to generate an aromatics product stream and a raffinate stream.

3. The process of claim 1 wherein the hydrocarbon feedstream comprises a full boiling range naphtha.

4. The process of claim 1 wherein the first reforming reactor system comprises a plurality of reactors.

5. The process of claim 4 wherein the plurality of reactors comprises a heater for each reactor to heat the reactor feedstream.

6. The process of claim 4 wherein the first reactor of the first reforming reactor system is operated at an inlet temperature between 440° C. and 560° C., and the subsequent reactors of the first reactor system are operated at inlet temperatures between 540° C. and 580° C.

7. The process of claim 4 wherein the plurality of reactors are in series with inter-reactor heaters.

8. The process of claim 1 wherein the second reforming reactor system comprises a plurality of reactors.

9. The process of claim 1 further comprising:
    passing the aromatics effluent stream to a reformate splitter to generate a reformate splitter overhead stream comprising C7 and C6 aromatics, and a reformate splitter bottoms stream comprising C8 and heavier aromatics; and
    passing the reformate splitter overhead stream to an aromatics separation unit thereby generating an aromatics product stream and a raffinate stream.

10. The process of claim 9 further comprising passing the raffinate stream to the dehydrogenation reactor.

11. A process for increasing the yields of aromatics from a hydrocarbon feedstream, comprising:
    passing the hydrocarbon feedstream to a fractionation unit to generate an overhead stream comprising C7 and lighter hydrocarbons, and a bottoms stream comprising C8 and heavier hydrocarbons;
    passing the overhead stream and a recycle gas to a dehydrogenation reactor to generate a dehydrogenated overhead stream;
    passing the bottoms stream and a portion of the recycle gas to a first reforming reactor system to generate a first reactor effluent having an increased aromatic content;
    passing the first reactor effluent to a second reforming reactor system, and the dehydrogenated overhead stream to the second reforming reactor system to generate an aromatics effluent stream, wherein the second reforming reactor is operated at an inlet temperature greater than or equal to a first reforming reactor inlet temperature and wherein the second reforming reactor system is operated at an inlet temperature greater than 540° C. and a pressure less than 580 kPa; and
    passing the aromatics effluent stream to a reformate splitter to generate a reformate splitter overhead stream comprising C7 and C6 aromatics, and a reformate splitter bottoms stream comprising C8 and heavier aromatics; and
    passing the reformate splitter overhead stream to an aromatics separation unit thereby generating an aromatics product stream and a raffinate stream.

12. The process of claim 11 further comprising passing the raffinate stream to the dehydrogenation reactor.

13. The process of claim 11 wherein the hydrocarbon feedstream is a full boiling range naphtha.

14. The process of claim 11 wherein the first reforming reactor system comprises at least two reactors, and where the first reactor in the first reforming reactor system is operated at an inlet temperature between 440° C. and 460° C., and wherein the subsequent reactors in the first reforming reactor system are operated at inlet temperatures between 540° C. and 580° C.

15. The process of claim 11 wherein the second reforming reactor system comprises a plurality of reactors and inter-reactor heaters.

16. The process of claim 11 wherein the second reforming reactor system is operated at an inlet temperature between 540° C. and 580° C.

\* \* \* \* \*